US00PP37583P3

(12) United States Plant Patent
Skotak, Jr.

(10) Patent No.: US PP37,583 P3
(45) Date of Patent: Aug. 11, 2026

(54) ***GUZMANIA* PLANT NAMED 'GM9309'**

(50) Latin Name: ***Guzmania* hybrid.**
Varietal Denomination: GM9309

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 1 day.

(21) Appl. No.: 19/393,340

(22) Filed: Nov. 18, 2025

(65) Prior Publication Data

US 2026/0157250 P1 Jun. 4, 2026

(30) Foreign Application Priority Data

Nov. 26, 2024 (QZ) ..... PBR 2024/2796

(51) Int. Cl.
*A01H 5/02* (2018.01)
*A01H 5/12* (2018.01)
*A01H 6/22* (2018.01)

(52) U.S. Cl.
USPC ..... Plt./371
CPC ..... *A01H 6/225* (2018.05); *A01H 5/02* (2013.01); *A01H 5/12* (2013.01)

(58) Field of Classification Search
USPC ..... Plt./371
CPC ..... A01H 6/225; A01H 5/02
See application file for complete search history.

*Primary Examiner* — Keith O. Robinson
(74) *Attorney, Agent, or Firm* — James R. Holm; Plant Novelty Rights, LLC

(57) ABSTRACT

A new and distinct *Guzmania* plant named 'GM9309' particularly distinguished by compact growth habit with a rosette diameter significantly smaller than the seed parent, with shorter, arching leaves forming a symmetrical, well-balanced rosette; upper bracts that are vivid red with a subtle pink overlay and a glossy surface, maintaining strong coloration under indoor conditions for an extended period; a central flower spike that is sturdy and remains upright, with white tubular flowers contrasting attractively with the red bracts; excellent postproduction longevity with bracts that retain color and firmness for several weeks longer than either of its parents; and uniform propagation with plants consistent in size, bract color, and growth habit.

2 Drawing Sheets

Figure 1:
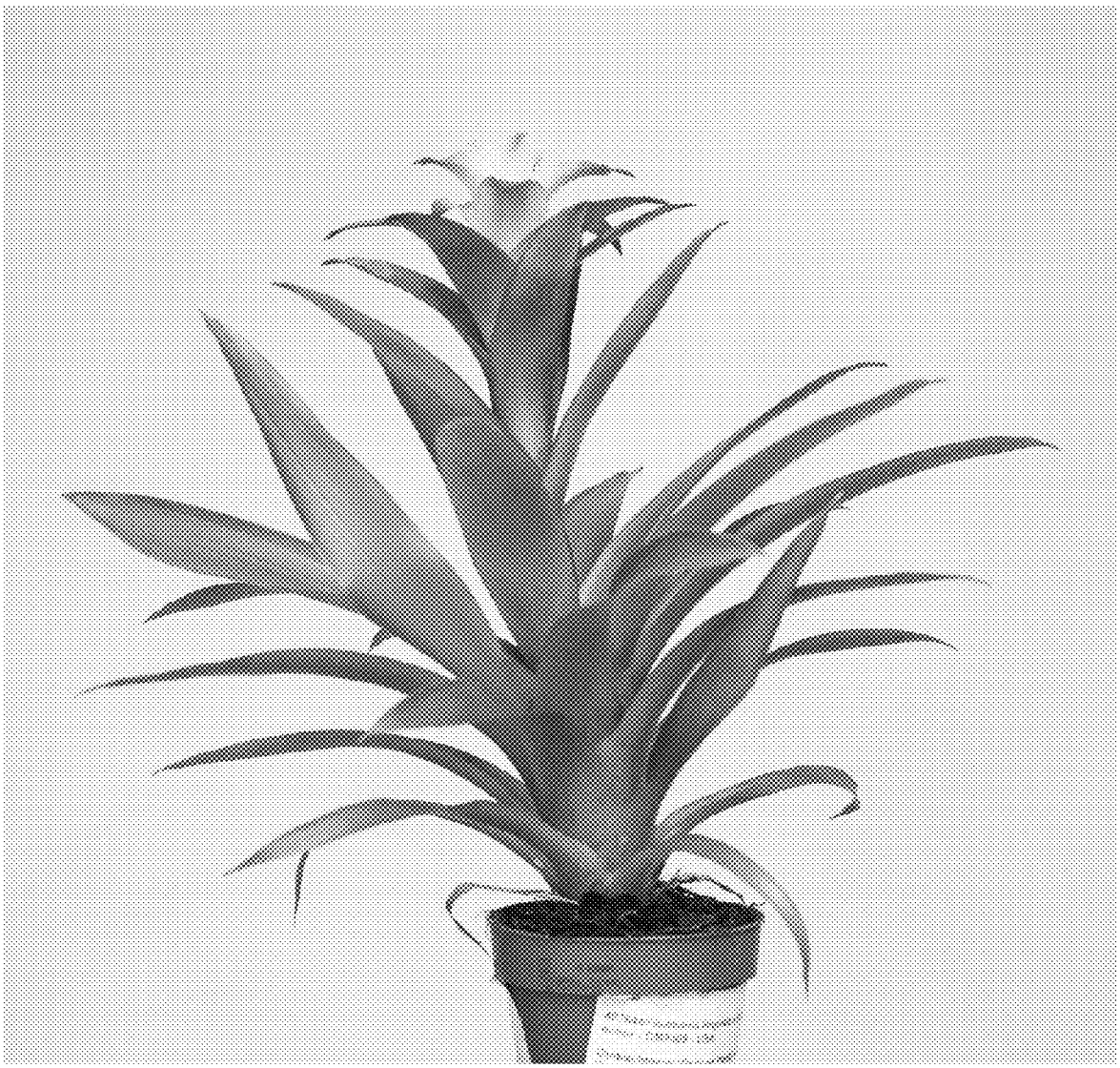

Genus and species: *Guzmania* hybrid.
Variety denomination: 'GM9309'.

STATEMENT REGARDING PRIOR DISCLOSURES BY THE INVENTOR

This application claims priority to CPVO application no. 2024/2796 filed on Nov. 26, 2024, which is herein incorporated by reference. The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Guzmania* plant, botanically known as *Guzmania* hybrid, and hereinafter referred to by the variety name 'GM9309'. The new *Guzmania* variety 'GM9309' is an F1 hybrid seedling selection which resulted from a controlled pollination breeding program. In May of 2016, the inventor performed the controlled cross-pollination of *Guzmania* hybrid 'Depladia' (U.S. Expired U.S. Plant Pat. No. 13,577), the seed parent, and *Guzmania wittmackii* 'Pink' (not patented), the pollen parent, at a commercial greenhouse in Alajuela, Costa Rica. Those skilled in the art recognize that

*Guzmania* seed can be difficult to germinate. Therefore, in September of 2016, the seed that resulted from the cross of May 2016 in Alajuela, Costa Rica were shipped by the inventor to a tissue culture laboratory in Evergem, Belgium for in vitro seed germination to increase the germination rate. At the direction of the inventor, the resulting seedlings were grown for 6 months to evaluate plant vigor and the most vigorous seedlings were then shipped back to Alajuela, Costa Rica for further evaluation by the inventor. In May of 2019, the inventor selected one seedling for further evaluation due to its unique growth habit and flower characteristics. This seedling was further evaluated for several years to confirm the distinctness and stability of the characteristics first observed. Upon confirmation this new and distinctive cultivar was given the name 'GM9309'.

The new *Guzmania* cultivar 'GM9309' was first reproduced asexually by meristematic tissue culture in January 2021 at a commercial laboratory in Evergem, Belgium. Asexual propagation by meristematic tissue culture of the new variety has shown that the unique features of the new variety are stable and reproduced true-to-type to date through 14 successive generations.

SUMMARY OF THE INVENTION

The new *Guzmania* cultivar 'GM9309' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Guzmania* cultivar. The combination of these characteristics distinguishes 'GM9309' as a new and distinct variety of *Guzmania*.

1. *Guzmania 'GM*9309' exhibits a compact growth habit with a rosette diameter significantly smaller than the seed parent, with shorter, arching leaves forming a symmetrical, well-balanced rosette.
2. *Guzmania 'GM*9309' exhibits upper bracts that are vivid red with a subtle pink overlay and a glossy surface, maintaining strong coloration under indoor conditions for an extended period.
3. *Guzmania 'GM*9309' exhibits a central flower spike that is sturdy and remains upright, with white tubular flowers contrasting attractively with the red bracts.
4. *Guzmania 'GM*9309' exhibits excellent postproduction longevity with bracts that retain color and firmness for several weeks longer than either of its parents.
5. *Guzmania 'GM*9309' exhibits uniform propagation with plants consistent in size, bract color, and growth habit.

DESCRIPTION OF THE PHOTOGRAPHS

This new *Guzmania* cultivar is illustrated by the accompanying-colored photographs which show the overall appearance and distinct characteristics of the plant. The colors shown are as true as can be reasonably obtained by conventional photographic procedures. The photographs are of 2-year-old plants grown in 10.5-centimeter circular containers in a conventional glass greenhouse in Evergem, Belgium. Colors in the photographs may differ slightly from the color values cited in the botanical description which accurately describes the colors of the new variety.

FIG. 1. shows the overall plant form, foliage, and inflorescence of 'GM9309'.

Figure 2:
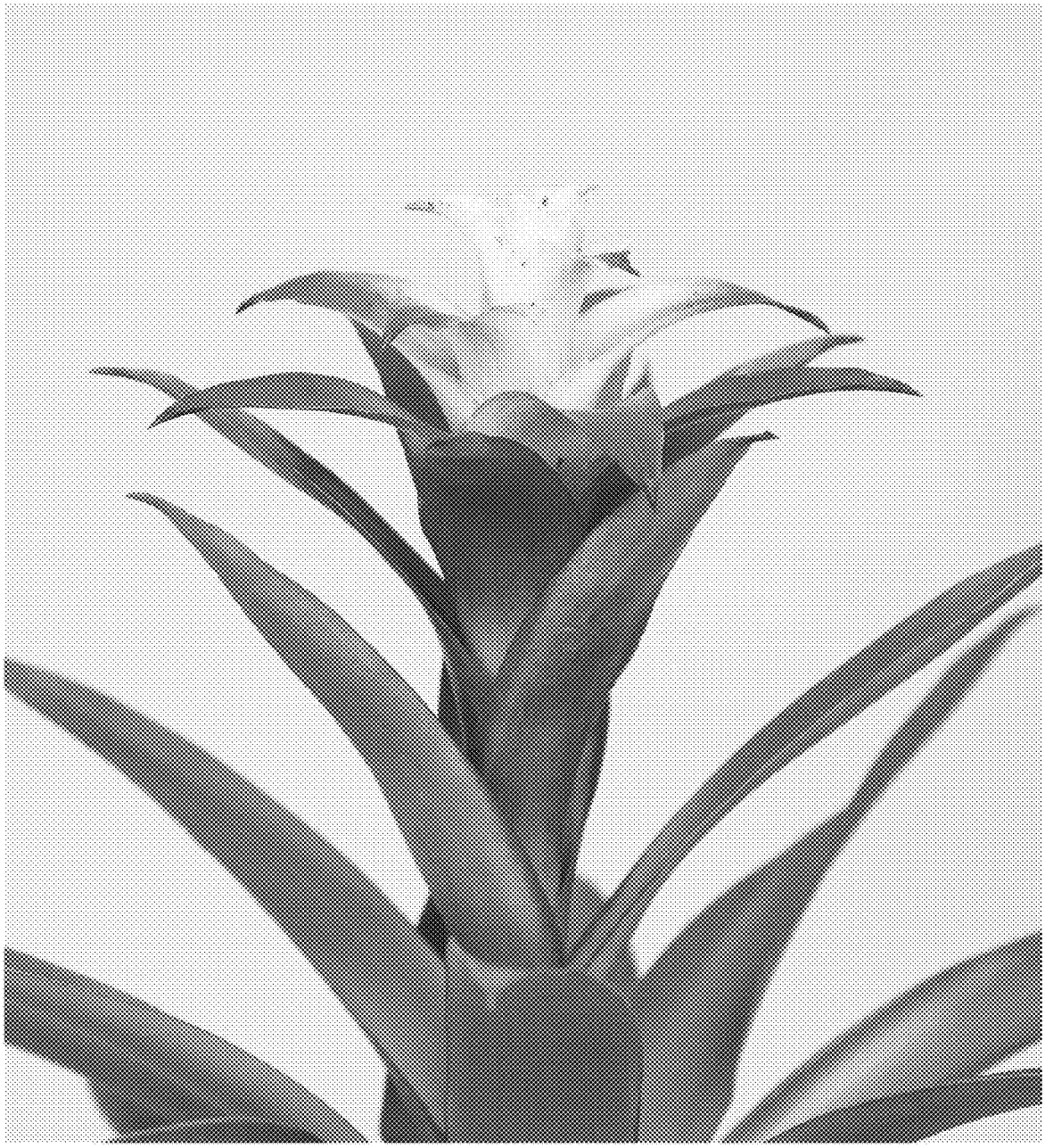

FIG. 2. shows a close-up of a typical inflorescence of 'GM9309'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a commercial greenhouse located in Evergem, Belgium. Plants were grown under maximum light levels of approximately 12,000 lux. Plants were maintained with a regular fertigation program and regularly watered with overhead irrigation. Detailed descriptions were taken in November 2025 from 2-year-old plants grown in 10.5-centimeter circular containers. Measurements and numerical values represent averages of typical plant types.

DETAILED BOTANICAL DESCRIPTION

Classification:

*Family*.—Bromeliaceae.

*Botanical*.—*Guzmania* hybrid.

*Denomination*.—'GM9309'.

General description:

*Growth habit*.—Perennial; basal rosette, inflorescence grow from the center of the basal rosette.

*Overall plant shape*.—Flattened globular with inflorescence carried slightly to well above the foliar plane.

*Height from soil level to top of foliar plane*.—26.0 cm.

*Height from soil level to top of floral plane*.—29.0 cm.

*Plant diameter or area of spread*.—50.5 cm.

*Growth rate*.—Moderate.

*Plant vigor*.—Moderate.

*Branching habit*.—Basal branching with no lateral branching.

*Propagation type*.—Meristematic tissue culture.

*Time to produce a finished plant*.—Approximately 24 months from tissue culture.

Root description:

*General*.—Moderately fibrous, non-fleshy.

*Length*.—Average 5.3 cm.

*Width*.—Average 0.1 cm.

*Color*.—N200A (brown).

Foliage description:

*Arrangement*.—Rosulate.

*Division*.—Simple.

*Quantity of leaves per rosette*.—27.

*Lamina*.—Shape: Ensiform. Length (including sheath): Average 40.0 cm to 45.0 cm. Width: Average 3.7 cm. Aspect: Moderately concave, moderately curled downward, leaf tips are in a near horizontal angle. Apex shape: Acuminate. Base: Sheathing. Sheath length: 6.2 cm. Sheath width 6.1 cm. Sheath color: 160A and 160B (greyed-yellow), veined 185B (greyed-purple) towards the base of the leaf. Undulation: No undulation. Lobes: Unlobed. Texture: Upper surface: Smooth, glabrous. Lower surface: Smooth, glabrous. Rugosity: Non-rugose. Pubescence: Not present. Luster (both upper and lower surfaces): Moderately glossy. Color: Juvenile foliage: Upper surface: 144A (yellow green). Lower surface: 144A (yellow green). Mature foliage: Upper surface: Darker than a blend of 143A and 144A (green to yellow-green). Lower surface: A blend of 144A and 146B (yellow green). Venation: Pattern: Parallel. Color (mature leaves): Upper surface: A blend of 137B and 143A (green), closest to 137B. Lower surface: NN137C (green).

Inflorescence description:

*Type and form*.—Terminal spike, holding an average of 5 smaller spikes, consisting of an average of 7 individual flowers.

*Height*.—Average 7.9 cm, excluding peduncle.

*Diameter*.—Average including bracts, 14.2 cm; average excluding bracts 2.3 cm.

*Quantity of flowers*.—Average 35.

*Quantity of flowers and flower buds per plant*.—Average 35.

*Natural flowering season*.—Continuously.

*Time to flower or response time*.—6 months.

*Flower bud*.—Length: Average 1.5 cm. Diameter: 0.25 cm. Shape: Lanceolate. Texture: Smooth and glabrous. Luster: Moderately glossy.

*Flower*.—Shape: Lanceolate. Aspect: Upright. Habit: Moderate. Fragrance: Not fragrant. Vertical height: Average 0.3 cm. Horizontal diameter: Average 0.25 cm. Length (depth): Average 1.9 cm. Tube texture: Smooth and glabrous. Longevity: Average 4 weeks. Persistence: Persistent.

*Petals*.—Arrangement: Rotate. Quantity per flower: Average 3. Number of petal whorls: Average 1. Petal fusion: Not fused. Length: Average 0.7 cm. Width: Average 0.2 cm. Shape: Ovate, concave. Tip: Obtuse. Base: Cuneate. Margin: Entire. Margin undulation: Not undulated. Texture (both upper and lower surfaces): Smooth and glabrous. Rugosity: Non-rugose. Luster (both upper and lower surfaces): Slightly glossy. Color when opening and fully opened: Upper surface: 1D (green-yellow). Lower surface: 154D (yellow-green). Venation: Inconspicuous. Petal color when fading (both upper and lower surfaces): Non-fading. Petaloids: Not present.

*Calyx*.—Shape: Rotate. Length: Average 1.9 cm. Diameter: 0.3 cm.

*Sepals*.—Arrangement: Rotate. Quantity per flower: Average 3. Quantity of sepal whorls: 1. Length: Average 1.9 cm. Width: Average 0.3 cm. Sepal fusion: Not fused. Shape: Lanceolate, strongly concave. Apex or tip: Narrow acuminate. Base: Cuneate. Margin: Entire. Texture (both upper and lower surfaces): Glabrous and smooth. Luster (both upper and lower surfaces): Moderately glossy. Color when opening and fully opened (both upper and lower surfaces): Transparent 155B (white). Sepal spurs: Not present.

*Peduncle*.—Terminal length: Average 21.2 cm. Terminal diameter: Average 0.8 cm. Angle: Vertical. Strength: Strong. Texture: Smooth and glabrous. Luster: Slightly glossy. Color: A blend of 150D and 157A (yellow-green to green-white).

*Bracts*.—At the base of each individual flower, a single fertile bract is present. Shape: Oblong, folded around flower. Length: Average 4.2 cm. Width: Average 1.9 cm when unfolded/open. Luster (both sides): Moderately glossy. Margin: Entire. Apex: Bluntly acute. Base: Broadly cuneate. Color (both upper and lower surfaces): 155D (transparent white).

*Bracts*.—Below each spike of individual flowers, a single bract is present. Shape: Lanceolate. Length (including sheath): Average 9.4 cm. Width: Average 2.9 cm. Luster (both sides): Moderately glossy. Margin: Entire. Apex: Acuminate. Base: Sheathing. Sheath: Length: Average 4.2 cm. Width: Average 4.7 cm. Color: Upper surface: 162D (greyed-yellow). Lower surface: A blend of 151D (yellow-green) and 160A (greyed-yellow), fading to 161A and 162A (greyed-yellow) near the base. Lower bract color: Upper surface: 53A (red), fading to 143A (green) near the top and tipped with 183B (greyed-purple). Lower surface: 53C (red), fading to 143A (green) at the top and tipped 183B (greyed-purple). Upper bract color: Upper surface: A blend of 145C and 150D (yellow-green), fading to a transparent 157D (green-white) towards the margins and tipped with 53A (red). Lower surface: 150C (yellow-green), fading to a transparent 157D (green-white) towards the margins and tipped N45C (red).

*Reproductive organs*.—Quantity of stamens per flower: 6. Filament: Length: Average 0.4 cm. Color: 155C (white). Anther: Shape: Dorsifixed, narrow sagittate. Length: Average 0.3 cm. Width: Average 0.1 cm. Color: 155A (white). Pollen amount: None observed. Pistil: Quantity: 1. Length: Average 0.4 cm. Stigma: Shape: Cleft; 3 parted, stigmas fringed. Length: Average 0.1 cm. Diameter: Average 0.1 cm. Color: 155C (white). Style: Length: Average 0.3 cm. Color: 155D (white). Ovary color: 160C (greyed-yellow).

Temperature tolerances: USDA Zones 10 to 13; at least tolerant of temperatures to 40 degrees Celsius.

Rain tolerance: High.

Wind tolerance: High.

Disease and pest tolerance: No claims are made to any superior disease or insect resistance or tolerance.

COMPARISON WITH THE PARENT PLANTS

The new *Guzmania* cultivar 'GM9309' can be distinguished from its seed parent *Guzmania* 'Depladia' in the following characteristics described in Table 1 below.

TABLE 1

| Characteristic | 'GM9309' | 'Depladia' |
|---|---|---|
| Plant height (including inflorescence) | Approx. 45.0 cm to 50.0 cm | Approx. 35.0 cm to 40.0 cm |
| Plant habit | Upright and open, with arching leaves | Upright and compact |
| Leaf length | Approx. 40.0 cm to 45.0 cm | Approx. 30.0 cm to 35.0 cm |
| Leaf width | 3.5 cm to 4.0 cm | 3.0 cm to 3.5 cm |
| Leaf color (upper surface) | 143A and 144A (green to yellow-green) | 137C (medium green) |
| Bract shape | Elongated, lanceolate | Broad, ovate |
| Bract color (upper bracts) | 45A (red) | 9A (bright yellow) |
| Bract arrangement | Erect and vertically layered | Open and spreading |
| Inflorescence height above rosette | 20.0 cm to 25.0 cm | 15.0 cm to 20.0 cm |
| Flower color | 155C (creamy white) | 11D (pale yellow) |

The new *Guzmania* cultivar 'GM9309' can be distinguished from its pollen parent *Guzmania wittmackii* 'Pink' in the following characteristics described in Table 2 below.

TABLE 2

| Characteristic | 'GM9309' | 'Pink' |
|---|---|---|
| Plant height (including inflorescence) | Approx. 45.0 cm to 50.0 cm | Approx. 60.0 cm to 70.0 cm |
| Plant habit | Upright and open, with arching leaves | Tall and upright |
| Leaf length | Approx. 40.0 cm to 45.0 cm | Approx. 55.0 cm to 60.0 cm |
| Leaf width | 3.5 cm to 4.0 cm | 4.0 cm to 4.5 cm |
| Leaf color (upper surface) | 143A and 144A (green to yellow-green) | 137A (dark green) |
| Bract shape | Elongated, lanceolate | Narrow, elongated |
| Bract color (upper bracts) | 45A (red) | 52B (soft pink) |
| Bract arrangement | Erect and vertically layered | More open and spreading |
| Inflorescence height above rosette | 20.0 cm to 25.0 cm | 30.0 cm to 35.0 cm |
| Flower color | 155C (creamy white) | 155B (white) |
| Overall appearance | Compact plant habit with vivid red bracts | Taller plant habit with soft pink bracts |

COMPARISON WITH RELATED KNOWN VARIETY

The new *Guzmania* cultivar 'GM9309' can be distinguished from the related known variety of *Guzmania* 'Eden' (unpatented) in the following characteristics described in Table 3 below.

TABLE 3

| Characteristic | 'GM9309' | 'Eden' |
|---|---|---|
| Plant habit | Upright and open with arching leaves | More compact and symmetrical |
| Leaf length | Longer leaves, approx. 40.0 cm to 45.0 cm | Shorter leaves, approx. 30.0 to 35.0 cm |
| Leaf width | Moderately broad, 3.5 cm to 4.0 cm | Slightly narrower, 3.0 cm to 3.5 cm |
| Leaf color (upper surface) | 143A and 144A (green to yellow-green) | 137C (bright green) |
| Bract shape | Elongated, lanceolate | Shorter and more rounded |
| Bract color (upper bracts) | 45A (red) | 52B (pinkish red) |

TABLE 3-continued

| Characteristic | 'GM9309' | 'Eden' |
|---|---|---|
| Bract arrangement | More erect and layered vertically | More open and spreading |
| Inflorescence height above rosette | 20.0 cm to 25.0 cm above rosette | 15.0 cm to 20.0 cm |
| Flower color | 155C (creamy white) | 11D (pale yellow) |
| Overall appearance | Tall, elegant plant with vivid red bracts and dark green foliage | Compact, balanced plant with lighter bracts and foliage |

What is claimed is:

1. A new and distinct cultivar of *Guzmania* plant named 'GM9309', substantially as illustrated and described herein.

* * * * *